(12) United States Patent
Hipskind et al.

(10) Patent No.: US 8,569,286 B2
(45) Date of Patent: Oct. 29, 2013

(54) NOTCH PATHWAY SIGNALING INHIBITOR COMPOUND

(75) Inventors: Philip Arthur Hipskind, New Palestine, IN (US); Gregory Alan Stephenson, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/551,681

(22) Filed: Jul. 18, 2012

(65) Prior Publication Data

US 2013/0029972 A1 Jan. 31, 2013

Related U.S. Application Data

(60) Provisional application No. 61/560,486, filed on Nov. 16, 2011, provisional application No. 61/512,016, filed on Jul. 27, 2011.

(51) Int. Cl.
*C07D 401/04* (2006.01)
*A61K 38/05* (2006.01)
*A61P 35/00* (2006.01)
*A61P 35/02* (2006.01)

(52) U.S. Cl.
USPC ..................... 514/212.06; 540/522

(58) Field of Classification Search
USPC ..................... 540/522; 514/212.06
See application file for complete search history.

(56) References Cited

FOREIGN PATENT DOCUMENTS

| WO | WO 98/28268 A2 | 7/1998 |
|----|----------------|--------|
| WO | WO 99/67219 A1 | 12/1999 |
| WO | WO 2004/069826 A1 | 8/2004 |
| WO | WO 2005/023772 A1 | 3/2005 |
| WO | WO 2005/040126 A1 | 5/2005 |
| WO | WO 2007/110335 A1 | 10/2007 |
| WO | WO 2009/087130 A1 | 7/2009 |
| WO | WO 2011/060051 A1 | 5/2011 |

OTHER PUBLICATIONS

Grabher, et al., "Notch 1 activation in the molecular pathogenesis of T-cell acute lymphoblastic leukaemia," Nature Review Cancer, 6:347-359 (2006).
Weng, et al., "Activating Mutations of NOTCH1 in Human T Cell Acute Lymphoblastic Leukemia," Science, 306:269-271 (2004).
Park, et al., "Notch3 Gene Amplification in Ovarian Cancer," Cancer Research, 66:6312-6318 (2006).
Gast, et al., "Somatic alterations in the melanoma genome: a high-resolution array-based comparative genomic hybridization study," Genes, Chromosomes & Cancer, 49:733-745 (2010).
Westhoff, et al., "Alterations of the Notch pathway in lung cancer," PNAS, 106:22293-22298 (2009).
Ranganathan, et al., "Notch signalling in solid tumours: a little bit of everything but not all the time," Nature Review Cancer, 11:338-351 (2011) and Supplementary information S1 (table).
Shih, et al., "Notch signaling, gamma-secretase inhibitors, and cancer therapy," Cancer Research, 67:1879-1882 (2007).
Lynch, et al., "The Effect of Cytochrome P450 Metabolism on Drug Response, Interactions, and Adverse Effects" American Family Physician, 76(3):391-396 (2007).
Kopan, et al., "The Canonical Notch Signaling Pathway: Unfolding the Activation Mechanism" Cell, 137(2):216-233 (2009).
Weng, et al., "Multiple niches for Notch in cancer: context is everything," Current Opinions in Genetics & Development, 14:48-54 (2004).
Radtke, et al., "The Role of Notch in Tumorigenesis: Oncogene or Tumour Suppressor?," Nature Reviews Cancer, 3:756-767 (2003).

*Primary Examiner* — Bruck Kifle
(74) *Attorney, Agent, or Firm* — John C Demeter

(57) ABSTRACT

The present invention provides a compound, or a pharmaceutically acceptable salt or hydrate, and a pharmaceutical composition containing said compound, or a pharmaceutically acceptable salt or hydrate, useful as a Notch pathway signaling inhibitor for the treatment of cancer.

6 Claims, 1 Drawing Sheet

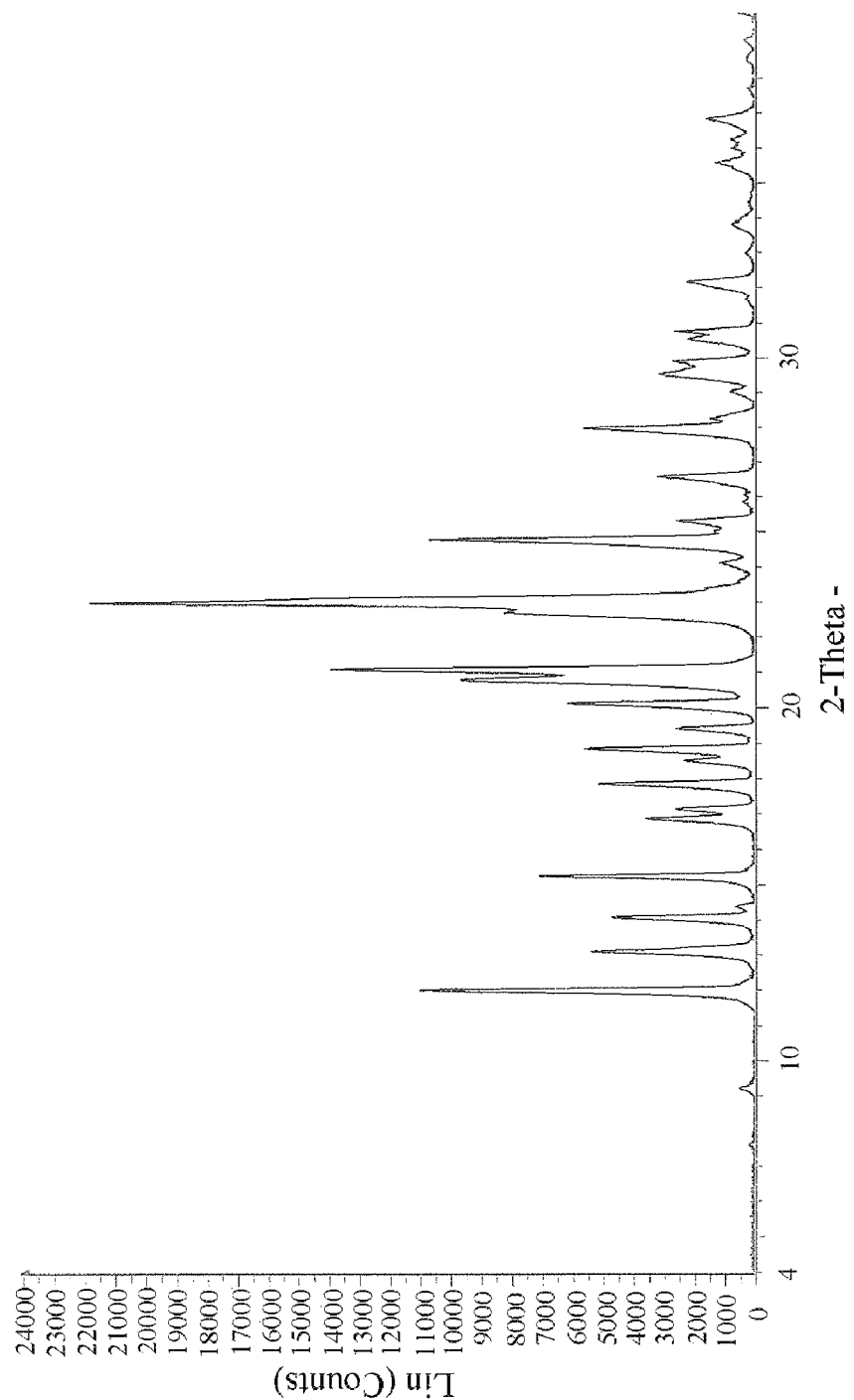

NOTCH PATHWAY SIGNALING INHIBITOR COMPOUND

Notch signaling is an evolutionary conserved pathway that plays an integral role in development and tissue homeostasis in mammals. The Notch receptors and ligands contain single-pass transmembrane domains, are expressed on the cell surface and, for that reason, Notch signaling is particularly important in mediating communication between adjacent cells expressing the receptors and ligands. There are four known Notch receptors found in rodents and humans, termed Notch 1 to Notch 4. The Notch receptors are heterodimeric proteins composed of extracellular and intracellular domains that are initially synthesized as a single polypeptide. Receptor-ligand interaction triggers a series of proteolytic cleavages of the Notch receptor polypeptide in which γ-secretase activity is involved. γ-Secretase activity cleaves Notch intracellular domain from the cell surface which translocates to the nucleus to form a transcription factor complex. Notch intracellular domain (NICD) is the active form of the protein. Various Notch signaling functions include proliferation, differentiation, apoptosis, angiogenesis, migration and self-renewal. These diverse roles of Notch signaling during the development and maintenance of normal tissues are aberrantly activated in different forms of cancer. The oncogenic functions of Notch signaling include the inhibition of apoptosis and the promotion of cell proliferation.

γ-Secretase plays a pivotal role in the Notch activation cascade. As a result, inhibitors of γ-secretase have been actively investigated for their potential to block Notch receptor activation. The compounds exemplified in WO 98/28268 such as 7C-203 are representative of such γ-secretase inhibitors. Despite the promise, no commercial Notch inhibitor chemotherapeutic agents have emerged.

There is a need to find compounds having Notch pathway signaling inhibitory activity. There is a further need to find compounds which have γ-secretase inhibitory activity. There is also a need to find compounds possessing distinct structural features that may contribute to Notch pathway signaling inhibition activity. There is a further need to find compounds demonstrating Notch pathway signaling inhibition activity and desirable in vivo distribution, metabolism and excretion properties.

FIG. 1 is a representative X-ray powder diffraction pattern for the compound of Example 2.

One aspect of the invention is to provide a Notch signaling inhibitor compound of the structure:

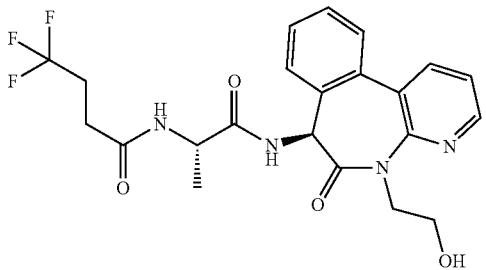

Compound 1 or a pharmaceutically acceptable salt or hydrate thereof.

A second aspect of the present invention provides a pharmaceutical composition comprising 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, in association with a pharmaceutically acceptable carrier. In a particular embodiment, the pharmaceutical composition comprises 4,4,4-trifluoro-N-[(1S)-2-[[(7S)-5-(2-hydroxyethyl)-6-oxo-7H-pyrido[2,3-d][3]benzoazepin-7-yl]amino]-1-methyl-2-oxo-ethyl]butanamide, or a pharmaceutically acceptable salt or hydrate thereof, together with a pharmaceutically acceptable carrier and optionally other therapeutic ingredients.

A third aspect of the present invention provides a method of inhibiting Notch signaling in a cancer patient in need thereof, comprising administering a therapeutically effective amount of, 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, to said patient.

A fourth aspect of the present invention provides a method of treating a cancer which is T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer or medulloblastoma in a patient comprising administering to a patient in need thereof a therapeutically effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

A fifth aspect of the present invention provides a method of treating a cancer which is T-cell acute lymphoblastic leukemia, acute lymphoblastic leukemia, chronic myelogenous leukemia, erythroleukemia, breast cancer, ovarian cancer, melanoma, pancreatic cancer, glioblastoma or colorectal cancer in a patient comprising administering to a patient in need thereof a therapeutically effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof.

A sixth aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for use in therapy.

A seventh aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for use in the treatment of a cancer which is T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer or medulloblastoma.

An eighth aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for use in the treatment of a cancer which is T-cell acute lymphoblastic leukemia, acute lymphoblastic leukemia, chronic myelogenous leukemia, erythroleukemia, breast cancer, ovarian cancer, melanoma, pancreatic cancer, glioblastoma or colorectal cancer.

A ninth aspect of the present invention provides use of a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for the manufacture of a medicament for the treatment of a cancer which is T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer or medulloblastoma.

A tenth aspect of the present invention provides use of a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, for the manufacture of a medicament for the treatment of a cancer which is T-cell acute lymphoblastic leukemia, acute lymphoblastic leukemia, chronic myelogenous leukemia, erythroleukemia, breast cancer, ovarian cancer, melanoma, pancreatic cancer, glioblastoma or colorectal cancer.

The term "patient" means mammal and "mammal" includes, but is not limited to, a human.

"Therapeutically effective amount" or "effective amount" means the dosage of the compound, or pharmaceutically acceptable salt or hydrate thereof, or pharmaceutical composition containing the compound, or pharmaceutically acceptable salt or hydrate thereof, necessary to inhibit Notch signaling in a cancer patient, and either destroy the target cancer cells or slow or arrest the progression of the cancer in a patient. Anticipated dosages of Compound 1 or a pharmaceutically acceptable salt or hydrate thereof are in the range of 0.1 to 200 mg/patient/day. Preferred dosages are anticipated to be in the range of 1 to 175 mg/patient/day. Most preferred dosages are anticipated to be in the range of 5 to 150 mg/patient/day. The exact dosage required to treat a patient and the length of treatment time will be determined by a physician in view of the stage and severity of the disease as well as the specific needs and response of the individual patient. Although expressed as dosage on a per day basis, the dosing regimen may be adjusted to provide a more optimal therapeutic benefit to a patient and to manage and ameliorate mucoid enteropathy (hypersecretion and accumulation of mucus in the gastrointestinal tract). In addition to daily dosing, dosing every other day (Q2D); every other day over a five day period followed by two days without dosing (T.I.W.); or every third day (Q3D) may be appropriate. A dosing regimen of every other day, T.I.W., or every third day is preferred along with administration (pre-, concomitant, or post-administration of Compound 1 of dexamethasone to manage or ameliorate mucoid enteropathy.

The terms "treatment," "treat," and "treating," are meant to include the full spectrum of intervention for the cancer from which the patient is suffering, such as administration of the active compound to alleviate to slow or reverse one or more of the symptoms and to delay progression of the cancer even if the cancer is not actually eliminated. The patient to be treated is a mammal, in particular a human being.

The compound of the present invention is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises 4,4,4-trifluoro-N-[(1S)-2-[[(7S)-5-(2-hydroxyethyl)-6-oxo-7H-pyrido[2,3-d][3]benzoazepin-7-yl]amino]-1-methyl-2-oxo-ethyl]butanamide, or a pharmaceutically acceptable salt or hydrate thereof, together with a pharmaceutically acceptable carrier and optionally other therapeutic ingredients particularly for treatment of cancer generally or a specific cancer type.

The compound of the present invention is capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

Compound 1, or a pharmaceutically acceptable salt or hydrate thereof, may be prepared by a variety of procedures known in the art, as well as those described below. The specific synthetic steps may be combined in different ways to prepare Compound 1, or a pharmaceutically acceptable salt or hydrate thereof.

Compound 1 is named: 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide; and may also be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide; and other names may be used to unambiguously identify Compound 1.

It will be understood Compound 1 is depicted as a single stereoisomer. There are two chiral centers giving rise to four stereoisomers. As used herein, references to Compound 1 are meant to also include racemic mixtures including Compound 1. Herein, the Cahn-Ingold-Prelog designations of (R)- and (S)- are used to refer to specific isomers. Specific stereoisomers can be prepared by stereospecific synthesis using enantiomerically pure or enriched starting materials. The specific stereoisomers of either starting materials, intermediates, or racemic mixtures including Compound 1 can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. While all mixtures containing the compound of the present invention are contemplated within the present invention, the preferred embodiment is Compound 1.

It has also been found that Compound 1 exists as atropisomers, or specific conformers. In aqueous solutions, 8-9% of atropisomer 2 (minor atropisomer) is detected by $^1$H NMR and LC-MS in equilibrium with atropisomer 1 (major atropisomer) at ambient temperature after 24 hours. In organic solvents, at ambient temperature after 24 hours, approximately 1-2% of atropisomer 2 is detected by $^1$H NMR and LC-MS in equilibrium with atropisomer 1. Although detectable by $^1$H NMR and LC-MS analysis, atropisomer 2 is not isolable.

The compounds employed as initial starting materials in the synthesis of the compound of the present invention are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5th Edition, Michael B. Smith and Jerry March, Wiley Interscience, 2001; Advanced Organic Chemistry, 4th Edition, Part B, Reactions and Synthesis, Francis A. Carey and Richard J. Sundberg, Kluwer Academic/Plenum Publishers, 2000, etc., and references cited therein.

The intermediates and Compound 1 are named using a SymaxDraw version 3.2 Drawing Program, from the structures, as the IUPAC name consistently applied.

PREPARATION 1

Benzyl (2S)-2-(4,4,4-trifluorobutanoylamino)propanoate

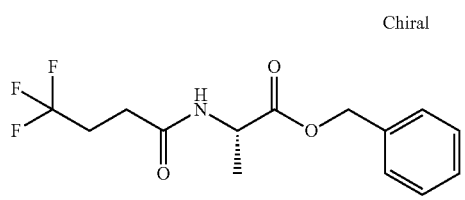 [SMILES: C[C@H](NC(=O)CCC(F)(F)F)C(=O)OCc1ccccc1]

Add successively L-alanine benzyl ester hydrochloride (7.00 g, 32.5 mmol), diisopropylethylamine (28.30 mL, 162.3 mmol), 1-hydroxybenzotriazole hydrate (7.46 g, 48.7 mmol) and 1-(3-dimethylaminopropyl)-3-ethylcarbodiimide hydrochloride (9.33 g 48.7 mmol) to a solution of 4,4,4-trifluorobutyric acid (7.131 g, 48.7 mmol) in dichloromethane (162 mL) at ambient temperature under nitrogen and stir for 20 hours. Add a 20% aqueous solution of citric acid (150 mL, 162 mmol), stir mixture for 5 minutes and separate layers. Extract from aqueous with dichloromethane (100 mL). Wash combined organics with saturated aqueous solution of sodium bicarbonate (150 mL), dry over magnesium sulfate and concentrate. Purify the residue by flash chromatography, eluting with hexane:ethyl acetate (4:1 to 2:1) to give the title compound as a white solid (9.22 g, 30.4 mmol, 94%). MS (m/z): 304 (M+1); $[\alpha]_{Na}^{25}=-44.6°$ (c=5.0, methanol).

PREPARATION 2

(2S)-2-(4,4,4-Trifluorobutanoylamino)propanoic acid

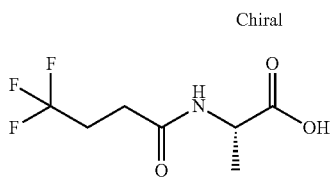

Add palladium/carbon (5%, 1.76 g, 0.8 mmol) in one portion to a solution of benzyl (2S)-2-(4,4,4-trifluorobutanoylamino)propanoate (8.80 g, 29 mmol) in methanol (88 mL) at ambient temperature. Degas the mixture (vacuum/nitrogen), fill with hydrogen (one atmosphere) and stir under hydrogen (29 mmol) for 5 hours. Filter through Celite®, rinse filter cake with methanol and concentrate the filtrate to obtain the title compound as a white solid (6.11 g, 28.7 mmol, 99%). MS (m/z): 214 (M+1); $[\alpha]_{Na}^{25}=-24.7°$ (c=5.0, methanol).

PREPARATION 3

Methyl 2-(2-bromophenyl)acetate

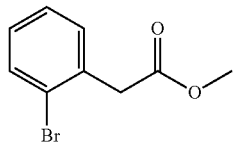

Add dimethylformamide (2.1 mL, 27.3 mmol) followed by thionyl chloride (52.3 mL, 717.8 mmol) over 7 minutes to a solution of 2-bromophenylacetic acid (150.0 g, 683.6 mmol) in dichloromethane (1.50 L) cooled with an ambient temperature water bath. Stir mixture for 5 hours, add methanol (41.5 mL, 1.0 mol) over 5 minutes. Bubble nitrogen through solution overnight. Concentrate to obtain the title compound as a colorless oil in quantitative yield (166.0 g, 724.7 mmol). $^1$H NMR (300 MHz, CDCl$_3$): 7.57 (d, J=7.9 Hz, 1H), 7.30-7.26 (m, 2H), 7.19-7.12 (m, 1H), 3.80 (s, 2H), 3.72 (s, 3H).

PREPARATION 4

Methyl 2-[2-(4,4,5,5-tetramethyl-1,3,2-dioxaborolan-2-yl)phenyl]acetate

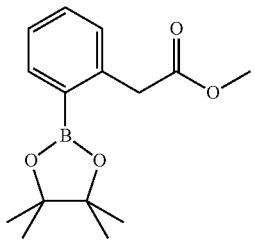

Degas a suspension of methyl 2-(2-bromophenyl)acetate (156.6 g, 684 mmol), bis(pinacolato)diboron (194.9 g, 752 mmol), and potassium acetate (135.6 g, 1.4 mol) in N-methylpyrrolidone (940 mL) with three vacuum/nitrogen cycles. Add (1,1'-bis(diphenylphosphino)ferrocene)palladium(II) chloride (11.4 g, 13.7 mmol) and heat at 80° C. After 15 hours add (1,1'-bis(diphenylphosphino)ferrocene)palladium(II) chloride (11.4 g, 13.7 mmol) and stir at 90° C. for 24 hours. Cool to ambient temperature and pour over a mixture of ice and water (3 L), and methyl tertiary butyl ether (1 L) was added. Stir mixture, filter through a pad of Celite® and separate layers. Extract from aqueous with methyl tertiary butyl ether (2×500 mL). Wash combined organics with water (2×500 mL), brine (500 mL), dry over sodium sulfate and concentrate. Purify the residue by flash chromatography, eluting with hexane:ethyl acetate (9:1) to give the title compound as a white solid (160.6 g, 581.6 mmol, 85%). MS (m/z): 277 (M+1).

PREPARATION 5

5,7-Dihydropyrido[2,3-d][3]benzazepin-6-one

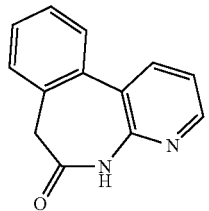 [SMILES: O=C1Cc2ccccc2-c2cccnc2N1]

Add potassium carbonate (235.7 g, 1.71 mol) to a solution of 2-amino-3-bromopyridine (88.5 g, 511.7 mmol) in 1,4-dioxane (550 mL) and water (550 mL). Degas the mixture with three cycles of vacuum/nitrogen, add palladium (II) acetate (6.4 g, 28.4 mmol) and tri-t-butylphosphonium tetrafluoroborate (16.5 g, 56.9 mmol) and stir under nitrogen at 88° C. Add a solution of methyl 2-[2-(4,4,5,5-tetramethyl-1,3,2-dioxaborolan-2-yl)phenyl]acetate (157.0 g, 568.5 mmol) in 1,4-dioxane (550 mL) dropwise over three minutes and stir the mixture at 88° C. for 20 minutes. Cool mixture to 50° C., add water (100 mL), and separate layers. Extract from aqueous with ethyl acetate (2×100 mL), dry combined organics over sodium sulfate and concentrate. Dissolve the concentrated material in N-methylpyrrolidone (314 mL), cool in ice bath and add sulfuric acid (314 mL, 5.9 mol) dropwise to maintain a temperature of approximately 45° C. Stir mixture at 140° C. for 90 minutes. Cool to ambient temperature, add ice (4 kg) and basify with portion wise addition of 50% aqueous NaOH solution until solution is pH 7-8. Cool suspension to 10-15° C., filter out solids and wash with water (2 L), hexanes (1 L) and methyl tertiary butyl ether (1 L). Dry under vacuum at 40° C. Treat material with refluxing mixture of 10% methanol/dichloromethane solution and filter hot (×4). Concentrate combined filtrates to afford the title compound as a light brown solid (85 g, 404.3 mmol, 71%). MS (m/z): 211 (M+1).

PREPARATION 6

5-[2-(tert-Butyl(dimethyl)silyl)oxyethyl]-7H-pyrido[2,3-d][3]benzazepin-6-one

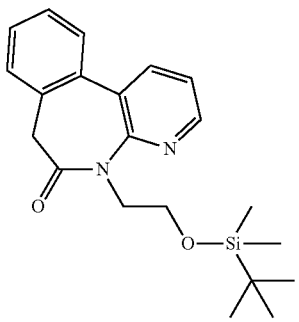 [SMILES: CC(C)(C)[Si](C)(C)OCCN1C(=O)Cc2ccccc2-c2cccnc21]

Add cesium carbonate (186.6 g, 572.7 mmol), (2-bromoethoxy)-tert-butyldimethylsilane (88.0 mL, 409.1 mmol), and sodium iodide (6.1 g, 40.9 mmol) to a suspension of 5,7-dihydropyrido[2,3-d][3]benzazepin-6-one (86.0 g, 409.1 mmol) in dimethylformamide (860 mL) and stir at 70° C. for 20 hours. Cool mixture to ambient temperature, pour over ice and water (100 mL), add ethyl acetate (200 mL). Filter mixture through Celite®, then wash with ethyl acetate (100 mL). Separate layers of filtrate, extract from aqueous with ethyl acetate (2×50 mL). Wash combined organics with water (2×100 mL), brine (100 mL), dry over sodium sulfate and concentrate. Dissolve material in tetrahydrofuran (1.28 L), add Silia® bond palladium scavenger (16.7 g) and stir at ambient temperature for 20 hours. Filter through a pad of silica, wash with tetrahydrofuran (200 mL) and concentrate to obtain the title compound (155 g, 420.6 mmol) as a light brown oil that crystallizes in quantitative yield. MS (m/z): 369 (M+1).

Method 2:

Heat a mixture 5,7-dihydropyrido[2,3-d][3]benzazepin-6-one (22.5 g, 106.9 mmol) and dimethylformamide (500 mL) to 100° C. for 5 minutes. Cool to 40° C., add cesium carbonate (104.3 g, 320.1 mmol) and (2-bromoethoxy)-tert-butyldimethylsilane (29.9 mL, 138.9 mmol) and stir at ambient temperature overnight. Heat to 60° C. for approximately 2 hours, and then cool to ambient temperature. Partition the residue between ethyl acetate (1 L) and water (3 L), back extract from aqueous layer with ethyl acetate (2×500 mL), wash combined organics with brine (2×500 mL). Dry combined organics over sodium sulfate and concentrate. Purify the residue by flash chromatography, eluting with ethyl acetate:hexane (0:100 to 100:0) to give the title compound as an oil (39.4 g, 106.9 mmol, 89%). MS (m/z): 369 (M+1).

PREPARATION 7

5-[2-(tert-Butyl(dimethyl)silyl)oxyethyl]-7-hydroxyimino-pyrido[2,3-d][3]benzazepin-6-one

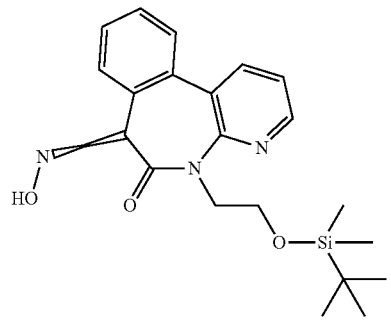

Add potassium 2-methylpropan-2-olate (66.1 g, 588.8 mmol) to a solution of 5-[2-(tert-butyl(dimethyl)silyl)oxyethyl]-7H-pyrido[2,3-d][3]benzazepin-6-one (155.0 g, 420.6 mmol) in tetrahydrofuran (1.6 L) at −5° C. and stir for 10 minutes. Add isoamyl nitrite (61.9 mL, 462.6 mmol) dropwise at −5° C. and stir mixture for 10 minutes. Pour over ice/water (2 L) and extract with ethyl acetate (3×200 mL). Wash combined organics with brine (200 mL), dry over sodium sulfate. Add toluene (1 L) and concentrate (×3) to obtain the title compound as a thick brown oil (160.0 g, 402.5 mmol, 96%). MS (m/z): 398 (M+1).

PREPARATION 8

(7S)-7-Amino-5-(2-hydroxyethyl)-7H-pyrido[2,3-d][3]benzazepin-6-one

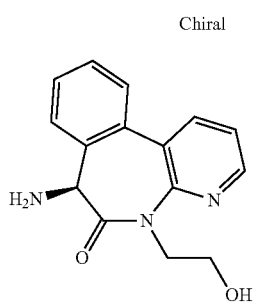 [SMILES: N[C@@H]1C(=O)N(CCO)c2ncccc2-c2ccccc21]

Add trifluoroacetic acid (124.0 mL, 1.64 mol) in several portions to a solution of 5-[2-(tert-butyl(dimethyl)silyl)oxyethyl]-7-hydroxyimino-pyrido[2,3-d][3]benzazepin-6-one (155.0 g, 389.9 mmol) in a mixture of dichloromethane (620 mL) and methanol (310 mL) in an ambient temperature water bath. Add zinc (76.5 g, 1.2 mol) in several portions so that internal temperature was maintained at 33-38° C. Stir for 15 hours at ambient temperature. Filter mixture through Celite®, wash with 10% methanol/dichloromethane (100 mL) and concentrate the filtrate. Add dichloromethane (0.5 L) and ice (500 g), stir and basify with a 50% aqueous solution of NaOH. Filter out solids, separate filtrate layers. Extract from aqueous with dichloromethane (2×100 mL), and concentrate combined organics. Slurry solids in hexane, and then filter and dry under high vacuum to obtain the racemate of the title compound as a light yellow solid (74.0 g, 274.8 mmol, 71%). Purify the material on a Chiralpak® AD column eluting with ethanol (0.2% dimethethylamine): acetonitrile (0:100 to 100:0) to obtain the title compound (35.0 g, 130 mmol, 33.3%) as a white solid. MS (m/z): 270 (M+1); $[\alpha]_{Na}^{25} = +187.83°$ (c=6.9, methanol).

PREPARATION 9

7-Azido-5-[2-(tert-butyl(dimethyl)silyl)oxyethyl]-7H-pyrido[2,3-d][3]benzazepin-6-one

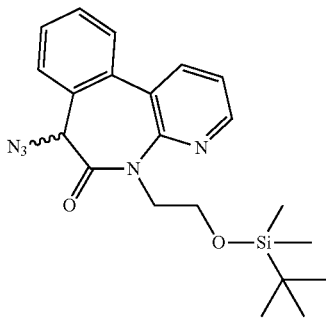 [SMILES: CC(C)(C)[Si](C)(C)OCCN1C(=O)C(N=[N+]=[N-])c2ccccc2-c2cccnc21]

Wash potassium hydride (approximately 2 scoops, 35 weight % in mineral oil) with hexanes and decant to remove oil, add tetrahydrofuran (60 mL) and cool to −78° C. Dry a solution of 2,4,6-tris(1-methylethyl)-benzenesulfonyl azide (37.6 g, 121.6 mmol) in tetrahydrofuran (60 mL) over sodium sulfate for 45 minutes. Decant azide solution into the potassium hydride suspension over 15 minutes. Remove cold bath and allow it to warm to ambient temperature for 45 minutes; set aside dry solution. Cool a solution of diisopropylamine (17.0 mL, 121.0 mmol) and tetrahydrofuran (50 mL) to −78° C., add n-butyl lithium (52.1 mL, 130.3 mmol) dropwise over 5 minutes. Remove cold bath and allow it to warm for 15 minutes then cool back to −78° C. Cannulate into a −78° C. solution of 5-[2-(tert-butyl(dimethyl)silyl)oxyethyl]-7H-pyrido[2,3-d][3]benzazepin-6-one (34.3 g, 93.1 mmol) in tetrahydrofuran (400 mL) over 5-10 minutes. Stir for one hour at −78° C. then remove cold bath and allow it to warm for 15 minutes (to approximately −45° C.). Cool to −78° C. and add the dried 2,4,6-tris(1-methylethyl)-benzenesulfonyl azide solution via cannula over 5-10 minutes. Remove bath and allow to warm to −5 to 0° C. over 1 hour. Cool in ice/water bath and add acetic acid (26.7 mL, 465.3 mmol) dropwise over 13 minutes. Allow to warm to ambient temperature over 65 minutes and quench with saturated sodium bicarbonate solution (14 Dilute reaction with ethyl acetate (600 mL) and water (2 L), separate layers, back extract from aqueous with ethyl acetate (2×400 mL). Wash combined organics with saturated aqueous sodium bicarbonate solution (500 mL) and brine (500 mL), dry over sodium sulfate and concentrate. Purify the residue by flash chromatography, eluting with ethyl acetate:hexane (0:100 to 100:0) to give the title compound as an oil (39.8 g, 92.3 mmol, 99%). MS (m/z): 410 (M+1).

PREPARATION 10

7-Amino-5-[2-(tert-butyl(dimethyl)silyl)oxyethyl]-7H-pyrido[2,3-d][3]benzazepin-6-one

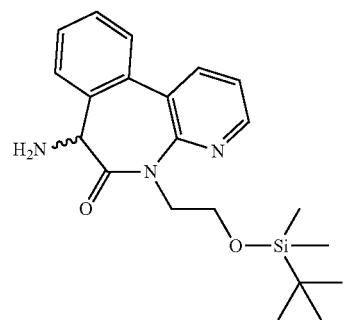 [SMILES: CC(C)(C)[Si](C)(C)OCCN1C(=O)C(N)c2ccccc2-c2cccnc21]

Add palladium/carbon (2.2 g, 1.0 mmol, 5% on carbon) to a nitrogen purged solution of 7-azido-5-[2-(tert-butyl(dimethyl)silyl)oxyethyl]-7H-pyrido[2,3-d][3]benzazepin-6-one (39.8 g, 92.3 mmol) in ethanol (923 mL). Evacuate/fill with hydrogen three times and stir under hydrogen (one atmosphere) at ambient temperature overnight. Filter over Celite®, rinse with ethanol and ethyl acetate and concentrate to obtain the title compound as a transparent oil (36.6 g, 89.9 mmol, 97%). MS (m/z): 384 (M+1).

PREPARATION 11 tert-Butyl N-[(1S)-2-[[5-[2-(tert-butyl(dimethyl)silyl)oxyethyl]-6-oxo-7H-pyrido[2,3-d][3]benzazepin-7-yl]amino]-1-methyl-2-oxo-ethyl]carbamate

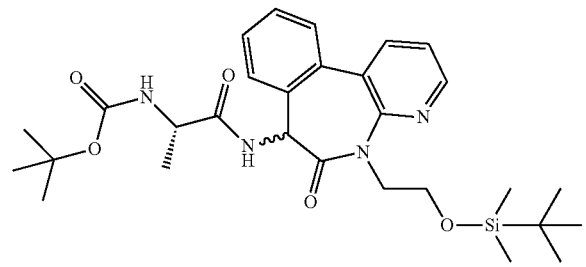 [SMILES: C[C@H](NC(=O)OC(C)(C)C)C(=O)NC1C(=O)N(CCO[Si](C)(C)C(C)(C)C)c2ncccc2-c2ccccc21]

Cool a mixture of 7-amino-5-[2-(tert-butyl(dimethyl)silyl)oxyethyl]-7H-pyrido[2,3-d][3]benzazepin-6-one (36.3 g, 89.9 mmol), dichloromethane (360 mL), triethylamine (16.3 mL, 116.9 mmol), 3-hydroxytriazolo[4,5-b]pyridine (15.9 g, 116.9 mmol), and (2S)-2-(tert-butoxycarbonylamino)propanoic acid (22.5 g, 116.9 mmol) to 0° C. Add 1-(3-dimethylaminopropyl)-3-ethylcarbodiimide hydrochloride (22.4 g, 116.9 mmol) and after 5 minutes allow to warm to ambient temperature overnight. Wash with water (500 mL×2), saturated aqueous sodium bicarbonate solution (2×300 mL), brine (300 mL), and then dry over sodium sulfate and concentrate. Purify the residue by flash chromatography, eluting with isopropyl alcohol:hexane (5:95 to 10:90) to give the title compound as a white foam (43.14 g, 77.77 mmol, 86.50%). MS (m/z): 555 (M+1).

PREPARATION 12

(2S)-2-Amino-N-[5-(2-hydroxyethyl)-6-oxo-7H-pyrido[2,3-d][3]benzazepin-7-yl]propanamide

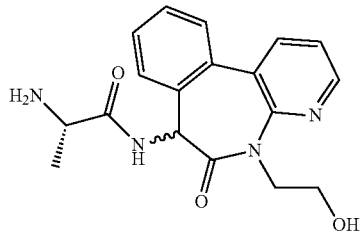 [SMILES: C[C@H](N)C(=O)NC1C(=O)N(CCO)c2ncccc2-c2ccccc21]

Add trifluoroacetic acid (30 mL, 396.76 mmol) over 5 minutes to a 0° C. solution of tert-butyl N-[(1S)-2-[[5-[2-(tert-butyl(dimethyl)silyl)oxyethyl]-6-oxo-7H-pyrido[2,3-d][3]benzazepin-7-yl]amino]-1-methyl-2-oxo-ethyl]carbamate (5.56 g, 10.0 mmol) and dichloromethane (30 mL) and allow to warm and stir at ambient temperature for 5 hours. Purify the residue by flash chromatography via SCX® columns (Isolute SCX-2×6) eluting with methanol followed by ethyl acetate: methanol (2N ammonia) (1:1) to obtain the title compound as a white solid (3.48 g, 10.2 mmol) in quantitative yield. MS (m/z): 341 (M+1).

EXAMPLE 1

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide

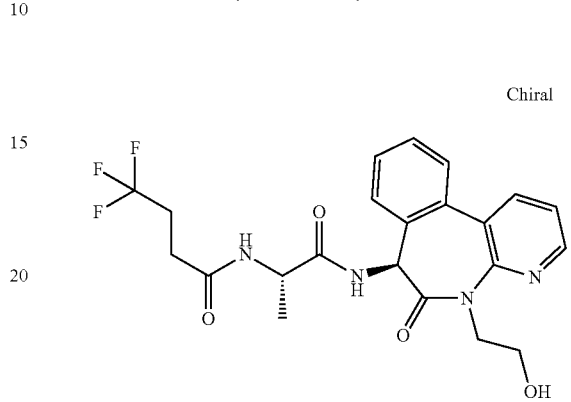

Add (2S)-2-(4,4,4-trifluorobutanoylamino)propanoic acid (28.9 g, 135.7 mmol; prepared substantially as described above in Preparation 2), 1-(3-dimethylaminopropyl)-3-ethylcarbodiimide hydrochloride (29.7 g, 155.1 mmol) sequentially to a suspension of (7S)-7-amino-5-(2-hydroxyethyl)-7H-pyrido[2,3-d][3]benzazepin-6-one (34.8 g, 129.2 mmol) in dichloromethane (696 mL) at 0° C., stir for 5 minutes. Add 1-hydroxybenzotriazole monohydrate (24.7 g, 155.1 mmol), allow it to stir for one hour, and then warm to ambient temperature. Add (2S)-2-(4,4,4-trifluorobutanoylamino)propanoic acid (0.6 g, 2.6 mmol) and stir for 15 minutes at ambient temperature. Add water (600 ml), filter out white solid, and separate layers of filtrate. Wash organic layer with water (3×200 mL), dry over sodium sulfate and concentrate to afford a light brown foam. Slurry material in 50% methyl tertiary butyl ether hexanes (500 mL), filter out solids, dry under high vacuum to obtain 65 g solids.

Add water (195 mL) and potassium bicarbonate (14.0 g, 140.0 mmol) to a 10° C. solution of the previously obtained solids (65.0 g, 140.0 mmol) in methanol (195 mL) and stir at ambient temperature for 29 hours. Concentrate and extract with dichloromethane (3×50 mL). Wash combined organics with water (3×20 mL), dry over sodium sulfate and concentrate. Purify the residue by flash chromatography eluting with methanol:dichloromethane (98:2, 7N in ammonia). Triturate material from 50% methyl tertiary butyl ether/hexane, then triturate from methyl tertiary butyl ether (500 ml). Wash solids with methyl tertiary butyl ether (200 mL) and hexane (200 mL) and dry solids under high vacuum to obtain the title compound as an off-white solid (42.0 g, 90.4 mmol, 65%). MS (m/z): 270 (M+1); $[\alpha]_{Na}^{25}$=−153.40° (c=5.0, methanol).
Method 2:
Add 1-(3-dimethylaminopropyl)-3-ethylcarbodiimide hydrochloride (2.50 g, 13.0 mmol) to a 0° C. mixture of (2S)-2-amino-N-[5-(2-hydroxyethyl)-6-oxo-7H-pyrido[2,3-d][3]benzazepin-7-yl]propanamide (3.4 g, 10.0 mmol), dichloromethane (40 mL), 3-hydroxytriazolo[4,5-b]pyridine (1.8 g, 13.0 mmol), 4,4,4-trifluorobutanoic acid (1.9 g, 13.0 mmol), and triethylamine (1.8 mL, 13.0 mmol). Allow to stir and warm to ambient temperature overnight. Add water (40 mL) and partition between dichloromethane (100 mL) and water (50 mL). Separate layers, back extract from aqueous with dichloromethane, wash combined organic layers with saturated aqueous sodium bicarbonate solution (2×100 mL). Back extract from bicarbonate layers with dichloromethane (25 mL), dry combined organic layers over sodium sulfate and concentrate. Purify the residue by flash chromatography, eluting with methanol (2N ammonia): dichloromethane (0:100 to 5:95) to give 3.77 g of the diastereomeric mixture. Material was purified on a Chiralpak® AD column eluting with ethanol (0.2% dimethethylamine): acetonitrile (0:100 to 100:0) to obtain the title compound as white solid (1.7 g, 3.7 mmol, 37%). MS (m/z): 465 (M+1).

PREPARATION 13

Methyl 2-(2-bromophenyl)acetate

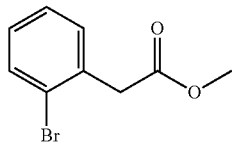

Combine 2-bromophenylacetic acid (500.0 g, 2.33 mol) with methanol (5.0 L) under a nitrogen atmosphere. Add concentrated sulfuric acid (185.8 mL) drop-wise at 20-35° C., and then warm to 60-65° C. with stirring for 3-4 hours. Cool the reaction mixture to 45° C. and concentrate under reduced pressure below 45° C. to a volume of approximately 750 mL. Cool the reaction mixture to 10-30° C. and add dichloromethane (2.5 L). Adjust the pH to 7-8 with sodium hydroxide (7%, 380.0 mL) and separate the layers. Concentrate the organic phase to dryness under reduced pressure below 45° C. to obtain the title compound (516.5 g, 97.0%) as a yellow oil.

PREPARATION 14

5,7-Dihydropyrido[2,3-d][3]benzazepin-6-one

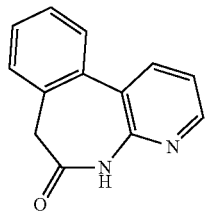 [SMILES: O=C1Cc2ccccc2-c2cccnc2N1]

Combine methyl 2-(2-bromophenyl)acetate (1.0 kg, 4.36 mol), dioxane (11.0 L), and N-methyl-2-pyrrolidone (7.0 L) with stirring at room temperature. Add bis(pinacolato)diboron (1.2 kg, 4.58 mol) and potassium acetate (855.9 g, 8.72 mol) to the mixture, and then degas the solution by passing nitrogen gas through the solution for 2-3 hours. Charge [1,1'-bis(diphenylphosphino)ferrocene]palladium(II) dichloride dichloromethane adduct (71.2 g, 97.2 mmol) under an atmosphere of nitrogen and then heat the reaction mixture to 80-90° C. for 18-20 hours to obtain methyl 2-[2-(4,4,5,5-tetramethyl-1,3,2-dioxaborolan-2-yl)phenyl]acetate as a solution which is used without isolation. Cool the reaction mixture to 15-25° C. and add 2-amino-3-bromopyridine (675.0 g, 3.90 mol) and a solution of potassium phosphate tribasic (2.41 kg, 11.3 mol) in water (3.0 L). Degas the solution by passing nitrogen gas through the solution for 2-3 hours, and add [1,1'-bis(diphenylphosphino)ferrocene]palladium(II) dichloride dichloromethane adduct (106.8 g, 130.8 mmol), then heat the reaction mixture to 80-90° C. for 18-40 hours. Cool the reaction mixture to 50-60° C., and slowly add a solution consisting of saturated sodium bicarbonate (13.0 L), saturated sodium chloride (13.0 L), and water (13.0 L). Stir the mixture for 2-3 hours at 50-60° C., cool to 15-25° C. and stir for an additional 18-20 hours. Filter the resulting solids and wash the filter cake with water (2×2.0 L). Transfer the solids to a clean reaction vessel, add ethyl acetate (5.0 L), and heat the mixture to 60-70° C. for 2-3 hours. Cool the solution to 15-25° C. and stir it for 1-2 hours and filter the resulting solids. Wash the filter cake with ethyl acetate (2×750 mL) and dry the resulting solids under vacuum to provide the title compound (644.0 g, 68.1%) as an off-white solid.

PREPARATION 15

5-[2-(tert-Butyl(dimethyl)silyl)oxyethyl]-7H-pyrido[2,3-d][3]benzazepin-6-one

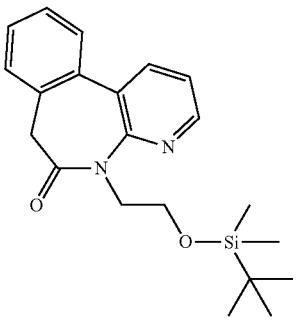 [SMILES: CC(C)(C)[Si](C)(C)OCCN1C(=O)Cc2ccccc2-c2cccnc21]

Add 5,7-dihydropyrido[2,3-d][3]benzazepin-6-one (33.8 g, 0.16 mol) in acetonitrile (340.0 mL) and stir at 20-30° C. for 0.5-1 hour. Add cesium carbonate (104.6 g, 0.32 mol) and (2-bromoethoxy)-tert-butyldimethylsilane (42.2 g, 0.18 mol) and heat the reaction mixture to 70-80° C. for 18-20 hours. Cool the reaction mixture to 20-25° C. and filter through diatomaceous earth (50.6 g). Wash the filter cake with acetonitrile (2×50.6 mL) and concentrate the filtrate under reduced pressure to arrive at a total volume of approximately 67.5 mL. Add toluene (152 mL), active carbon (2.53 g) and heat the mixture to 60-70° C. for 1-2 hours. Cool the mixture to 25-35° C. and filter the reaction mixture over diatomaceous earth (50.6 g). Rinse the filter cake with toluene (17.0 mL) and concentrate under reduced pressure to obtain the title compound as a light brown oil that crystallizes on standing (56.8 g, 92.2%).

PREPARATION 16

5-[2-(tert-Butyl(dimethyl)silyl)oxyethyl]-7-hydroxyimino-pyrido[2,3-d][3]benzazepin-6-one

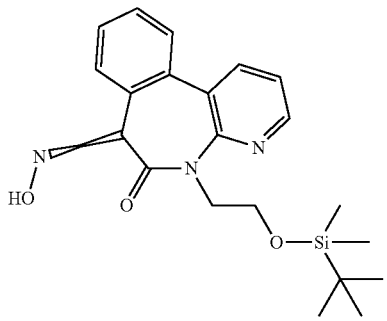

Combine 5-[2-(tert-butyl(dimethyl)silyl)oxyethyl]-7H-pyrido[2,3-d][3]benzazepin-6-one (30.0 g, 0.08 mol) and toluene (300.0 mL), cool the reaction mixture to −10-0° C. Add potassium tert-butoxide (18.2 g, 0.16 mol), isoamyl nitrite (13.34 g, 0.11 mol) and then stir for 3-5 hours. Transfer the reaction mixture to a cool (0-5° C.) biphasic solution of ethyl acetate (210 mL) and water (510 mL) and stir for 15-30 minutes. Warm the reaction mixture to 15-25° C. and separate the layers. Extract the aqueous layer with additional ethyl acetate (120 mL) and methyl tert-butyl ether (120 mL) and combine the organic layers. Concentrate the organic under reduced pressure to a solution volume of approximately 60-90 mL and then add toluene (240 mL) and ethyl acetate (75 mL). Filter the solution through silica gel (45.0 g), rinse the silica gel with a mixture of toluene (210 mL) and ethyl acetate (60 mL), and concentrate the filtrate under reduced pressure to a volume of approximately 75 mL. Add heptane (120 mL) and concentrate the mixture to a volume of approximately 60 mL and filter the resulting solids. Wash the filter cake with heptane (25 mL) and dry under vacuum to provide the title compound (28.3 g, 72.5%) as a yellow solid.

PREPARATION 17

7-Amino-5-[2-(tert-butyl(dimethyl)silyl)oxyethyl]-7H-pyrido[2,3-d][3]benzazepin-6-one

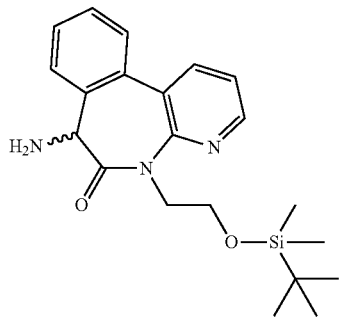

Combine 5-[2-(tert-butyl(dimethyl)silyl)oxyethyl]-7-hydroxyimino-pyrido[2,3-d][3]benzazepin-6-one (206.0 g, 0.52 mol) and tetrahydrofuran (2.3 L) into an autoclave under an atmosphere of nitrogen. Add Raney nickel (232.0 g, 1.13 wt/wt equivalents) to the reaction mixture and introduce hydrogen atmosphere (87 psi). Stir the reaction mixture at 60-65° C. for 24 hours. Filter the mixture over diatomaceous earth and wash the filter aid with tetrahydrofuran (500 mL). Concentrate the filtrate to obtain the title compound (196.0 g, 93.2%) as a brown oil. MS (m/z): 384 (M+1).

PREPARATION 18 tert-Butyl N-[(1S)-2-[[5-(2-hydroxyethyl)-6-oxo-7H-pyrido[2,3-d][3]benzazepin-7-yl]amino]-1-methyl-2-oxo-ethyl]carbamate

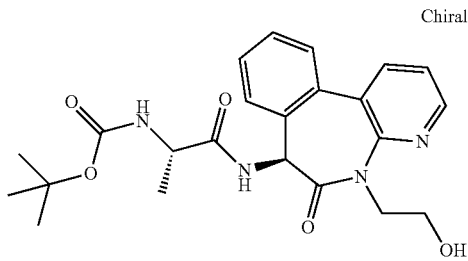 [SMILES: C[C@H](NC(=O)OC(C)(C)C)C(=O)N[C@@H]1C(=O)N(CCO)c2ncccc2-c2ccccc21]

Combine 7-amino-5-[2-(tert-butyl(dimethyl)silyl)oxyethyl]-7H-pyrido[2,3-d][3]benzazepin-6-one (166.0 g, 0.43 mol), dichloromethane (2.2 L), and L-Boc-alanine (106.4 g, 0.56 mol) under nitrogen atmosphere. Add hydroxybenzotriazole (1.46 g, 10.8 mmol) and triethylamine (102.5 mL, 0.74 mol) maintaining the internal temperature below 30° C. Add 1-ethyl-3-(3-dimethylaminopropyl)carbodiimide (128.2 g, 0.67 mol) in portions and stir for 16-18 hours at 20-30° C. Purify the reaction mixture by silica gel chromatography (300 g silica gel), eluting with dichloromethane (498 mL×2). Combine the dichloromethane solution and wash it with water (2×3.3 L). Concentrate the organic phase under reduced pressure to a volume of 300 mL to 400 mL and add ethyl acetate (664.0 mL). Concentrate the mixture under reduced pressure to a volume of 300-400 mL, and add ethyl acetate (664 mL). Concentrate the mixture under reduced pressure to a volume of 300-400 mL, and add ethyl acetate (1.3 L). Add tetra-n-butylammonium fluoride trihydrate (149.4 g, 0.47 mol) and stir for 16-18 hours at 20-30° C. Add an aqueous solution of sodium chloride (20%, 1.6 L), separate the layers, and wash the organic phase again with aqueous sodium chloride (20%, 1.6 L). Concentrate the organic to an approximate volume of 800-900 mL and stir the mixture for 12-16 hours at 20-30° C. Filter the resulting solids, wash the filter cake with ethyl acetate (91.3 mL). Purify the filtrate with silica gel chromatography (300 g silica gel), eluting with ethyl acetate (2×500 mL) to provide the title compound (82.6 g, 85.2% de, 100% ee, 51.2% yield) as a yellow oil. MS (m/z): 441 (M+1).

PREPARATION 19

(2S)-2-Amino-N-[(7S)-5-(2-hydroxyethyl)-6-oxo-7H-pyrido[2,3-d][3]benzazepin-7-yl]propanamide

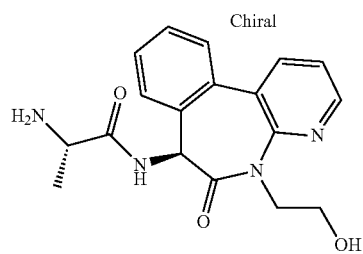 [SMILES: C[C@H](N)C(=O)N[C@@H]1C(=O)N(CCO)c2ncccc2-c2ccccc21]

Combine tert-butyl N-[(1S)-2-[[5-(2-hydroxyethyl)-6-oxo-7H-pyrido[2,3-d][3]benzazepin-7-yl]amino]-1-methyl-2-oxo-ethyl]carbamate (54.0 g, 0.12 mol) and acetonitrile (212.7 mL) under a nitrogen atmosphere. Add hydrochloric acid (317.5 mL, 4N, 1.27 mol) drop-wise to maintain the internal temperature below 30° C., and stir the reaction mixture for 16-18 hours at 20-30° C. Add water (324.0 mL) and dichloromethane (430 mL) and separate the layers. Discard the organic layer and to the aqueous phase add dichloromethane (645 mL) and adjust the pH to approximately 10 using aqueous sodium hydroxide (20%, 252 mL). Separate the layers, extract the aqueous layer with additional dichloromethane (2×430 mL), and combine the organic phases. Concentrate the organic under reduced pressure below 45° C. to an approximate volume of 130-150 mL, and add tetrahydrofuran (322 mL). Concentrate the solution under reduced pressure below 45° C. to an approximate volume of 200-220 mL, and add additional tetrahydrofuran (213 mL). Concentrate the reaction mixture under reduced pressure to an approximate volume of 250-270 mL, and heat to 60-65° C. for 2-3 hours. Cool the reaction mixture to 5-15° C. slowly and stir for 5-8 hours. Filter the resulting solids, wash the filter cake with ethyl acetate (56 mL). Transfer the solids to a clean reaction vessel, add ethyl acetate (150 mL), and heat to 60-65° C. for 2-3 hours, then cool the solution to 5-15° C. slowly. Stir for 2-3 hours at this temperature and collect the resulted solids by filtration. Wash the filter cake with ethyl acetate (45 mL) and dry the solids in an oven under reduced pressure below 60° C. to provide the title compound (21.0 g, 99.2% de, 100% ee, 51.0% yield) as an off white solid. MS (m/z): 341 (M+1).

EXAMPLE 2

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate

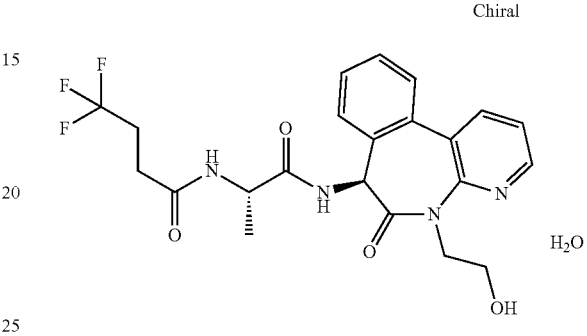

Combine (2S)-2-amino-N-[(7S)-5-(2-hydroxyethyl)-6-oxo-7H-pyrido[2,3-d][3]benzazepin-7-yl]propanamide (45.0 g, 132.2 mmol) and dimethylformamide (452.9 mL) under a nitrogen atmosphere. Cool to 0-5° C. and add N-ethyldiisopropylamine (77.4 mL, 444.0 mmol), 4,4,4-trifluorobutyric acid (19.9 g, 139.3 mmol), and hydroxybenzotriazole monohydrate (22.3 g, 153.1 mmol). Stir the solution for 5-10 min and add 1-ethyl-3-(3-dimethylaminopropyl)carbodiimide hydrochloride (30.6 g, 159.6 mmol) in one portion. Warm the reaction mixture to 20-25° C. and stir for 1-2 hour. Add ethyl acetate (1.4 L) and water (1.8 L) and stir for 0.5-1 hour. Separate the phases and wash the organic layer with an aqueous sodium bicarbonate solution (5%, 1.0 L) and concentrate the solution under reduced pressure to obtain a volume of 200-300 mL. Add ethanol (522 mL) and concentrate the solution under reduced pressure to obtain a volume of 200-300 mL. Repeat for three times. Add ethanol (180 mL) and 5% solution of potassium carbonate (34.6 mL) and stir for 0.5-1 hour at 20~25° C. Add water (667 mL) and seed crystals of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate (0.4 g, 0.86 mmol) (Seed crystals can be generated from the solids obtained from previous lots of the product, or can be obtained using other methods common known and used by one skilled in the art, such as recrystallization of a small aliquot) and stir for 2-3 hours at 20-25° C. Filter and wash the filter cake with a mixture of ethanol (63 mL) and water (42 mL) twice. Dry the resulting solids in an oven under reduced pressure below 40° C. to provide the title compound (41.9 g, 99.6% de, 100% ee, 65.3% yield) as a white to off white solid. MS (m/z): 465 (M-H$_2$O+1).

XRPD of Example 2

The XRPD patterns of crystalline solids are obtained on a Bruker D4 Endeavor X-ray powder diffractometer, equipped with a CuKα source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. (For example, see: U.S. Pharmacopia 33—National Formulary 28 Chapter <941> Characterization of Crystalline Solids by X-ray Powder Diffraction (XRPD) Official Oct. 1, 2010-Feb. 1, 2011). Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability oft 0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction pattern is collected at ambient temperature (19-25° C.) and relative humidity (20-60%).

Thus, a prepared sample of the compound of Example 2 is characterized by an XRPD pattern using CuKα radiation as having diffraction peaks (2-theta values) as described in Table 1 below. The form is crystalline and contains a peak at 22.97 degree in combination with one or more of the peaks selected from the group consisting of 11.96, 18.81, 20.78, and 21.07 degrees 2-theta, with a tolerance for the diffraction angles of 0.2 degrees.

TABLE 1

X-ray powder diffraction peaks of Example 2:

| Peak | Angle (2-Theta °) | Intensity % |
|---|---|---|
| 1 | 7.573 | 0.8 |
| 2 | 9.177 | 2.3 |
| 3 | 11.96 | 50.4 |
| 4 | 13.063 | 24.6 |
| 5 | 14.036 | 21.5 |
| 6 | 14.352 | 2.9 |
| 7 | 15.223 | 32.4 |
| 8 | 16.845 | 15.8 |
| 9 | 17.12 | 11.8 |
| 10 | 17.828 | 23.4 |
| 11 | 18.481 | 10.6 |
| 12 | 18.809 | 25.3 |
| 13 | 19.396 | 11.7 |
| 14 | 20.102 | 28 |
| 15 | 20.778 | 44.2 |
| 16 | 21.068 | 63.8 |
| 17 | 22.713 | 36.8 |
| 18 | 22.967 | 100 |
| 19 | 23.407 | 7.4 |
| 20 | 23.625 | 2.4 |
| 21 | 24.11 | 5.3 |
| 22 | 24.772 | 49 |
| 23 | 25.028 | 6.5 |
| 24 | 25.311 | 11.5 |
| 25 | 25.868 | 1.8 |
| 26 | 26.586 | 14.6 |
| 27 | 27.979 | 25.6 |
| 28 | 28.27 | 6.6 |
| 29 | 29.033 | 3.6 |
| 30 | 29.54 | 14.3 |
| 31 | 29.9 | 12.2 |
| 32 | 30.556 | 9.9 |

TABLE 1-continued

X-ray powder diffraction peaks of Example 2:

| Peak | Angle (2-Theta °) | Intensity % |
|---|---|---|
| 33 | 30.766 | 11.5 |
| 34 | 31.703 | 1.3 |
| 35 | 32.186 | 10.1 |
| 36 | 33.015 | 1.4 |
| 37 | 33.822 | 3.4 |
| 38 | 34.007 | 2 |
| 39 | 34.451 | 1.1 |
| 40 | 34.728 | 0.5 |
| 41 | 35.381 | 2.7 |
| 42 | 35.601 | 5.8 |
| 43 | 36.052 | 3.2 |
| 44 | 36.272 | 3.5 |
| 45 | 36.866 | 7.2 |
| 46 | 37.73 | 0.8 |
| 47 | 38.232 | 0.2 |
| 48 | 38.608 | 1.2 |
| 49 | 39.139 | 1.5 |

Solid State NMR of Example 2

$^{13}$C Cross polarization/magic angle spinning (CP/MAS) NMR (solid-state NMR or SSNMR) spectra are obtained using a Bruker Avance II 400 MHz NMR spectrometer (Lilly tag K299547) operating at a carbon frequency of 100.622 MHz and equipped with a Bruker 4 mm triple resonance probe (K299551). TOSS sideband suppression is used along with cross polarization employing SPINAL64 decoupling (70.8 Watts) and a RAMP100 shaped H-nucleus CP pulse. Acquisition parameters are as follows: 90° proton r.f. pulse width of 2.5 contact time was 3.5 ms, pulse repetition time of 5 s, MAS frequency of 10 kHz, spectral width of 30 kHz, acquisition time is 34 ms and the number of scans is 10,587. Chemical shifts are referenced to adamantane (δ=29.5 ppm) in a separate experiment. $^{13}$C NMR (solid-state): δ (ppm) 18.65, 27.52, 28.76, 47.66, 49.96, 55.02, 58.88, 122.87, 126.49, 129.73, 131.37, 132.31, 137.28, 145.01, 149.17, 168.53, 170.30, 175.55.

Karl Fischer Titration of Example 2

Karl Fischer titrations are obtained using a Brinkmann Methrohm 756 KF Coulometer. The control standard is determined using Hydranol® as a water standard in duplicate. Run the sample in triplicate and record the average percentage of water to determine the amount of water in a sample. Karl Fischer Titration average result of Example 2 is 3.9% water. Theoretic percentage of one molar equivalent of water in Example 2 is 3.7%.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenviroments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis (see http://www.sanger.ac.uk/genetics/CGP/Census) as well as the COSMIC (Catalogue of Somatic Mutations in Cancer) database of somatic mutations in human cancer (see http://www.sanger.ac.uk/genetics/CGP/cosmic). A further source containing abundant information on cytogenetic changes causally linked to various cancers is the Atlas of Genetics and Cytogenetics in Oncology and Haematology (http://atlasgeneticsoncology.org//Anomalies/Anomliste.html#MDS). These databases also include chromosomal aberrations for at least some of the malignancies of the present invention.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

The oncogenic role of Notch was first reported in human T-cell leukemia involving a translocation of the Notch1 intracellular domain to the T-cell receptor-β promoter region, resulting in the over expression of Notch1 intracellular domain (Grabher et al. *Nature Review Cancer,* 2006(6):347-359; Weng et al. *Science,* 2004(306):269-271). Over expression of Notch1 intracellular domain in hematopoietic progenitor cells of mice caused the mice to exhibit T-cell acute lymphoblastic leukemia similar to humans. In addition to T-cell acute lymphoblastic leukemia, there is increasing evidence that Notch signals are oncogenic in other cancers through multiple mechanisms including receptor amplification and over expression of ligands and/or receptors including acute lymphoblastic leukemia, acute myelogenous leukemia, chronic myelogenous leukemia and erythroleukemia. Aberrant constitutive Notch signaling due to mutation or over expression of ligands and/or receptors is also implicated in a number of solid tumor malignancies including breast cancer, ovarian cancer (Park et al. *Cancer Research,* 2006(66):6312-6318), melanoma (Gast et al. *Genes, Chromosomes & Cancer,* 2010(49):733-745), lung cancer, non small cell lung cancer (Westhoff et al. *PNAS,* 2009(106):22293-22298), pancreatic cancer, glioblastoma, colorectal cancer, head and neck cancer, cervical cancer, prostate cancer, liver cancer, squamous cell carcinoma (oral), skin cancer and medulloblastoma (Ranganathan et al., *Nature Review Cancer,* 2011 (11):338-351 and Supplementary information S1 (table)). Inhibition of Notch signaling presents an attractive target to provide therapeutic benefits to cancer patients whose disease was induced by aberrant activation of constitutive Notch signaling pathway. Shih et al. *Cancer Research,* 2007(67)1879-1882.

The following in vitro and in vivo studies demonstrate the Notch pathway signaling inhibitory activity and efficacy of Compound 1 against various specific cancer cell lines. These assays are generally recognized by those skilled in the art as indicative of human clinical chemotherapeutic activity. Inhibition of Notch intracellular domain cleavage by γ-secretase is believed to be effective against each of Notch 1, Notch 2, Notch 3 and Notch 4 receptors. Assays evidencing Notch pathway signaling inhibitory activity and efficacy may be carried out substantially as follows or by similar assays affording similar data.

Notch1 N1ICD Nuclear Accumulation Cellular Imaging Assay

HEK293ΔE12 cells (HEK293 cells are engineered to stably express mouse Notch 1 cDNA coding for amino acid 1703-2183, NP_032740.3, with 23 amino acid signal peptide sequence, MPRLLTPLLCLTLLPALAARGLR (SEQ ID NO:1), at its N-terminus) are plated at 5000 cells/well in 96 well plates, incubated in Dulbecco's Modified Eagle's Medium-high glucose with 5% fetal bovine serum at 37° C., 5% $CO_2$ for 24 hours. Cells are treated with test compound, dosing at 10 points of 1:3 dilutions across the range of 1000 nM to 0.05 nM, and with final dimethyl sulfoxide (DMSO) concentration at 0.2%. After 24 hours treatment, cell plates are processed through following steps sequentially: fix cells with 100 μl/well PREFER™ fixative for 30 minutes at room temperature (RT); permeablize cells with 100 μl/well 0.1% TRITON® X100 in phosphate buffered saline (PBS) for 20 min at RT; wash 3 times with 100 μl/well PBS each; add 50 μl/well rabbit anti-N1ICD (Notch1 Intracellular Domain) antibody, at 1:2000 in PBS with 1% bovine serum albumin and incubate 1.5 hours at 37° C.; wash 3 times with 100 μl/well PBS each; incubate with 50 μl/well goat anti-rabbit IgG Alexa 488 at 1:1000 dilution in PBS with 1% bovine serum albumin and incubate 1 hours at 37° C.; wash 3 times with 100 μl/well PBS each and add 100 μl/well 15 μM propidium iodide with 50 μg/ml RNAse for 30 minutes to stain nuclei. Plates are scanned with ACUMEN EXPLORER™ Laser-scanning fluorescence microplate cytometer (TTP LABTECH LTD) to measure total cell nuclear count/well and total nuclear area/well with fluorescence at 655 nm-705 nm (emission of DNA bound propidium iodide) and fluorescence of antibody binding to N1ICD in nuclear region at 505 nm-530 nm. The main assay output is a ratio of total fluorescence of nuclear N1ICD to total nuclear area, the normalized nuclear N1ICD signal. A relative cytotoxicity profiling was collected as % cell number to 0.2% DMSO control cells. The antibody that recognizes cleaved Notch 1 or N1ICD is raised to a human peptide corresponding to the amino terminal cleavage site of human Notch1 at Val1744. In untreated control cells, N1ICD generated from Notch1 will translocate and accumulate in nucleus. When cells are treated by a Notch 1 cleavage inhibiting compound, the signal of nuclear N1ICD will decrease. Concentration response and the $IC_{50}$ are determined by curve fitting to a four parameter logistic for the nuclear N1ICD signal, while the % cell number is plotted in the same graph for cytotoxicity profiling. Performing the assay essentially as described above, the average $IC_{50}$ for Compound 1 is 0.41 nM (n=7). The compound does not affect cell number up to 1000 nM concentration.

These data evidence Compound 1 has affinity for Notch 1 and inhibits the intracellular accumulation of the Notch 1 intracellular domain cell signaling peptide.

Inhibition of N1ICD cleavage in human tumor cell lines

To evaluate potency of Compound 1 in its ability to inhibit N1ICD cleavage, several human tumor cell lines are utilized. A2780 is a human ovarian cell line (Sigma-Aldrich, No. 93112519); MIA PaCa-2 is a human pancreas cell line (ATCC No. CRL-1420); BxPC-3 is a human pancreas cell line (ATCC No. CRL-1687); SW480 is a human colorectal cell line (ATCC No. CCL-228); HCT 116 is a human colorectal cell line (ATCC No. CCL-247); DLD-1 is a human colorectal cell line (ATCC No. CCL-221); MDA-MB-231 is a human mammary gland cell line (ATCC No. HTB-26); U-87 MG is a human glioblastoma cell line (ATCC No. HTB-14); A375 is a human malignant melanoma cell line (ATCC No. CRL-1619); CCRF-CEM is a human acute lymphoblastic leukemia (ALL) cell line (ATCC No. CCL-119); SUP-T1 is a human T-cell lymphoblastic leukemia cell line (ATCC No. CRL-1942); K-562 is a human chronic myelogenous leukemia (CML) cell line characterized by the presence of a fusion transcript comprised of the Bcr and Abl1 genes (ATCC No. CCL-243); Jurkat, Clone E6-1 is a human acute T-cell leukemia cell line (ATCC No. TIB-152); MOLT-3 is a human acute lymphoblastic leukemia (ALL) cell line (ATCC No. CRL-1552); MOLT-4 is a human acute lymphoblastic leukemia (ALL) cell line (ATCC No. CRL-1582); HEL 92.1.7 is a human erythroleukemia cell line (ATCC No. TIB-180). Each of the cell lines are obtained from the American Type Culture Collection (ATCC) at the ATCC number stated, except the A2780 cell line which is obtained from Sigma-Aldrich at the stated catalog number. The cells are grown in their respective culture media at 37° C. in 5% $CO_2$ with humidity in the atmosphere. Cell culture media for A2780 human ovarian carcinoma is RPMI-1640 (without phenol red) with 2.05 mM L-glutamine, added 2 mM L-glutamine, 0.01 mg/ml insulin and 10% fetal bovine serum (FBS); for HCT 116 human colorectal carcinoma is McCoy's 5A with 1.5 mM L-glutamine, 0.075% Na-bicarbonate and 10% FBS; for SW480 human colorectal carcinoma is RPMI-1640 with 2.05 mM L-glutamine, 20 mM HEPES and 10% FBS; U-87 MG human glioblastoma is Minimal Essential Medium/Earl's Balanced Salt Solution with 2 mM L-glutamine, 0.1 mM Non-essential amino acids (NEAA), 1 mM Na-pyruvate, and 10% FBS; for MIA PaCa-2 human pancreatic carcinoma is Dulbecco's Modified Eagles Medium (DMEM) without Na-pyruvate, with high glucose (4500 mg/ml), 4 mM L-glutamine, 2.5% horse serum and 10% FBS; for K-562 human CML is DMEM with high glucose (4500 mg/ml), 4 mM L-glutamine, 10 mM HEPES, 0.1 mM NEAA, 1 mM Na-pyruvate and 10% FBS; for Jurkat, Clone E6-1 human acute T cell leukemia is RPMI-1640 with 2.05 mM L-glutamine, 2.5 g/L glucose, 10 mM HEPES, 1 mM Na-pyruvate, 0.075% Na-bicarbonate and 10% FBS; for A-375 human malignant melanoma and MDA-MB-231 human breast adenocarcinoma is DMEM with high glucose (4500 mg/ml), 4 mM L-glutamine and 10% FBS; for BxPC-3 human pancreatic adenocarcinoma, DLD-1 human colorectal adenocarcinoma, SUP-T1 human lymphoblastic leukemia, MOLT-3 human ALL, Molt-4 human ALL, CCRF-CEM human ALL, and HEL 92.1.7 human erythroleukemia is RPMI-1640 with 2.05 mM L-glutamine, 2.5 g/L glucose, 20 mM HEPES, 1 mM Na-pyruvate, and 10% FBS. When 80-90% confluent, cells are treated with compound, dosing at 10 points of 1:3 dilutions across the range of 50 nM to 0.0025 nM, and with final dimethyl sulfoxide (DMSO) concentration at 0.01%. After 24 hours treatment, cell plates are processed essentially through the following steps sequentially: Cells are collected after trypsinization, washed once with ice-cold PBS, and lysed in 100 µl ice cold XY lysis buffer (25 mM Tris pH 7.5, 10 µg/ml Trypsin/Chymotrypsin inhibitor, 10 µg/ml Aprotinin, 60 mM Beta-glycerol phosphate, 1% Triton® X-100, 10 mM NaF, 2.5 mM pyrophosphate, 150 mM NaCl, 15 mM ethylene diamine tetra acetic acid (EDTA) pH 8.0, 5 mM ethylene glycol-bis(2-aminoethylether)-N,N,N',N'-tetra acetic acid (EGTA) pH 8.0, 1 mM Na Vanadate, 10 µg/ml Leupeptin, 1 mM dithiothreitol, 1 µM microcystin LR, 10 µg/ml N-p-tosyl-L-phenylalanine chloromethyl ketone (TPCK), 2 mM Na-p-tosyl-L-arginine methyl ester hydrochloride (TAME), 15 mM 4-nitrophenyl phosphate di(tris) salt (PNPP), 0.1 mM 4-(2-aminoethyl)benzenesulfonyl fluoride hydrochloride (AEBSF), 5 mM benzamidine, 1 µM Okadaic Acid) containing 1× Complete tablet (Roche Complete™ No. 11 697 498 001) and 1× Protease Inhibitor cocktail (Sigma Aldrich P8340). Lysate is incubated on ice for 15 min with brief vortexing every 5 min and sonicated for 1 minute on ice. Samples are spun in a 4° C. eppendorf centrifuge at 30,000 rpm for 30 minutes and 80 µl of supernatant is collected for analysis. Total protein concentration is determined using Pierce BCA Protein Assay Kit™ (Thermo Scientific, Rockford, Ill.) using a Thermomax™ plate reader (Molecular Devices, Sunnyvale, Calif.). N1ICD levels are determined using a custom N1ICD Enzyme Linked Immunosorbent Assay (ELISA). Analyte is captured with a cleaved Notch1 (Val1744)-specific custom rabbit monoclonal antibody and detected with a C-terminal Notch1 SULFO-TAG® (Meso Scale Diagnostics, Gaithersburg, Md.) polyclonal sheep antibody (R&D Systems, Minneapolis, Minn.). Lysates are diluted to 1 µg/µl in ice-cold ELISA tris lysis buffer R60TX (Meso Scale Diagnostics, Gaithersburg, Md.), containing 1× Complete tablet (Roche Complete™ mini No. 11 836 153 001) and 1× Protease Inhibitor cocktail (Sigma Aldrich P8340), and 25 µl is added to the ELISA plate. Incubation of 25 µg protein lysate is done at RT for one hour each to capture analyte and with detection antibody. Plates are read on a Sector Imager 6000™ (Meso Scale Discovery, Gaithersburg, Md.). Background subtracted N1ICD is normalized to total protein and presented as % inhibition relative to the vehicle-treated group. The $IC_{50}$ value is determined by fitting concentration response data to "4-parameter sigmoidal dose-response (variable slope)" model using GraphPad Prism® 4 software. The $IC_{50}$ value for Compound 1 in various tumor cell lines is shown in Table 1.

TABLE 1

| Cell Lines | $IC_{50}$ (nM) |
| --- | --- |
| A2780 | 1.03 |
| MIA PaCa-2 | 0.71 |
| BxPC-3 | 0.39 |
| SW480 | 0.10 |
| HCT 116 | 0.72 |
| DLD-1 | 0.98 |
| MDA-MB-231 | 0.50 |
| U-87 MG | 0.28 |
| A-375 | 0.48 |
| CCRF-CEM | 0.76 |
| SUP-T1 | 1.24 |
| K-562 | 0.74 |
| Jurkat | 5.95 |
| MOLT-3 | 0.61 |

TABLE 1-continued

| Cell Lines | IC$_{50}$ (nM) |
| --- | --- |
| MOLT-4 | 0.74 |
| HEL 92.1.7 | 0.23 |

The data in Table 1 evidences the potency of Compound 1 in its ability to inhibit N1ICD signaling peptide generation by inhibiting γ-secretase activity and as a result N1ICD signaling peptide accumulation in specific human tumor cell lines.

In-vivo Efficacy and Target Inhibition Studies
Animal Studies

To evaluate in vivo efficacy and effect of Compound 1 on inhibition of Notch processing pharmacodynamics (PD), several cell lines- and patient-derived xenograft models are used. A2780 (2×10$^6$), SW480 (6×10$^6$), HCT 116 (6×10$^6$), U-87 MG (6×10$^6$), and A-375 (10×10$^6$) cells in a 1:1 matrigel mix (0.2 mL volume) are implanted by subcutaneous injection in the hind leg of 6-8 weeks of age athymic nude female mice (Harlan Laboratories). K-562 (6×10$^6$) cells in a 1:1 matrigel mix (0.2 mL volume) are implanted by subcutaneous injection in the hind leg of 6-8 weeks of age CD1 nμ/nμ female mice (Charles River Laboratories). HEL 92.1.7 (7×10$^6$) in a 1:1 matrigel mix (0.2 mL volume) are implanted by subcutaneous injection in the hind leg of 6-8 weeks of age CB17 severely combined immune deficient female mice (Taconic Farms). Patient-derived tumors are minced into 1-2 mm pieces and mixed with matrigel (1:1) in 0.2 ml volume and implanted by subcutaneous injection in the hind leg of 6-8 weeks of age athymic nude female mice (Harlan Laboratories). Patients-derived tumor models include: human glioblastoma (EL2144), human triple negative invasive ductal breast carcinoma (EL1997), and human colon carcinoma (EL1989, EL 1986, and EL 2056) with samples obtained after patient consent and hospital approval from IU Health, Methodist Hospital, Indianapolis, Ind., USA 46206. A total of 7 to 10 mice are used for each group. Just before implantation for A2780, SW480, HEL 92.1.7, A-375, K-562, and patient-derived tumor models, animals are irradiated (450 Total Body Irradiation). Mice are fed ad libitum on normal chow. Treatment is initiated with oral administration (gavage) of compound or vehicle (1% Na-CMC in 0.25% Tween-80) in 0.2 mL volume when tumor size reached to 150±50 mm$^3$. At designated time points following treatment, animals are sacrificed by CO$_2$ asphyxiation and cervical dislocation. Tumors are removed and used for PD response analysis. Tumor growth and body weight are monitored over time to evaluate efficacy and signs of toxicity. Bidimensional measurements of tumors are performed twice a week and tumor volumes are calculated based on the following formula: (Tumor Volume)=[(L)×(W2)×(Π/6)] where L is mid-axis length and W is mid-axis width. Tumor volume data are transformed to a log scale to equalize variance across time and treatment groups. The log volume data are analyzed with a two-way repeated measures analysis of variance by time and treatment using the MIXED™ procedures in SAS™ software (version 8.2). The correlation model for the repeated measures is spatial power. Treated groups are compared to the control group at each time point. The MIXED™ procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time. Antitumor activity is expressed as tumor growth inhibition percentage (TGI %) and is calculated by comparing tumor volume in the treatment group with vehicle treatment group. Percentage Tumor Growth Inhibition (% TGI) and statistical significance value (p value) for Compound 1 is measured essentially as described above and summarized in Table 2.

N1ICD Analysis

To evaluate N1ICD levels in tumors, approximately 75 mg is cut from the frozen tumor and minced prior to homogenization (actual mass recorded). Frozen tumor samples are transferred to Lysing Matrix-D™ tubes and re-suspended in ice-cold XY lysis buffer (25 mM Tris pH 7.5, 10 μg/ml Trypsin/Chymotrypsin inhibitor, 10 μg/ml Aprotinin, 60 mM Beta-glycerol phosphate, 1% Triton® X-100, 10 mM NaF, 2.5 mM pyrophosphate, 150 mM NaCl, 15 mM ethylene diamine tetra acetic acid (EDTA) pH 8.0, 5 mM ethylene glycol-bis(2-aminoethylether)-N,N,N',N'-tetra acetic acid (EGTA) pH 8.0, 1 mM Na Vanadate, 10 μg/ml Leupeptin, 1 mM dithiothreitol, 1 μM microcystin LR, 10 μg/ml N-p-tosyl-L-phenylalanine chloromethyl ketone (TPCK), 2 mM Na-p-tosyl-L-arginine methyl ester hydrochloride (TAME), 15 mM 4-nitrophenyl phosphate di(tris) salt (PNPP), 0.1 mM 4-(2-aminoethyl)benzenesulfonyl fluoride hydrochloride (AEBSF), 5 mM benzamidine, 1 μM Okadaic Acid) containing 1× Complete tablet (Roche Complete™ No. 11697 498 001) and 1× Protease Inhibitor cocktail (Sigma-Aldrich P8340) at a mass:volume ratio of 75 mg/ml buffer. Tissues are homogenized in a Fast Prep FP120 homogenizer (Thermo Scientific, Rockford, Ill.) at a speed of 6.0 for 30 seconds at 4° C., followed by 15 minute incubation on ice. This is repeated for a total of 2-3 cycles until homogenization is complete. Lysates are spun in a 4° C. eppendorf centrifuge at 30,000 rpm for 15 minutes to remove debris. 400 μl of supernatant is removed and transferred to a new eppendorf tube and subjected to a freeze/thaw cycle. Samples are re-spun in a 4° C. eppendorf centrifuge at 30,000 rpm for 30 minutes and 120 μl of supernatant is collected for analysis. Total protein concentration is determined using Pierce BCA Protein Assay Kit™ (Thermo Scientific, Rockford, Ill.) using a Thermomax™ plate reader (Molecular Devices, Sunnyvale, Calif.). N1ICD levels are determined using a custom N1ICD ELISA. Analyte is captured with a cleaved Notch1(Val1744)-specific custom rabbit monoclonal antibody and detected with a C-terminal Notch1 SULFO-TAG™ (Meso Scale Discovery, Gaithersburg, Md.) polyclonal sheep antibody (R&D Systems, Minneapolis, Minn.). Lysates are diluted to 2 μg/μl in ice-cold ELISA tris lysis buffer (R6OTX) (Meso Scale Discovery, Gaithersburg, Md.) containing 1× Complete tablet (Roche Complete™ mini No. 11 836 153 001) and 1× Protease Inhibitor cocktail (Sigma-Aldrich P8340), and 25 μl is added to the ELISA plate. Incubation of 50 μg protein lysate is done at RT for one hour each to capture analyte and with detection antibody. Plates are read on a Sector Imager 6000™ (Meso Scale Discovery, Gaithersburg, Md.). Background subtracted N1ICD is normalized to total protein and presented as % inhibition relative to the vehicle-treated group. N1ICD % inhibition and statistical significance (p value) as measured by Dunett's method in tumors harvested 4 hours after last dose for Compound 1 is analyzed essentially as described above and summarized in Table 2.

TABLE 2

| Tumor Model | Dose (mg/kg) | Schedule | % TGI (p Value) | % N1ICD Inhibition (p Value) |
|---|---|---|---|---|
| A2780 | 10 | Q2Dx11 | 56.55 (<0.0001) | 68.5 (<0.0001) |
| A2780 | 10 | Q3Dx8 | 32.99 (<0.0001) | 55.3 (<0.0001) |
| A2780 | 3 | (BID)QDx7 + (BID)Q2Dx7 | 72.35 (<0.0001) | 50.7 (0.0004) |
| A2780 | 3 | QDx21 | 46.60 (<0.0001) | 62.8 (<0.0001) |
| A2780 | 10 | Q2Dx13 | 51.11 (<0.0001) | 74.8 (<0.0001) |
| A2780 | 8 | Q2Dx13 | 68.60 (<0.0001) | 71.7 (<0.0001) |
| A2780 | 7 | Q2Dx13 | 56.95 (<0.0001) | 65.9 (<0.0001) |
| A2780 | 6 | Q2Dx13 | 36.33 (<0.05 to <0.01) | 60.7 (<0.0001) |
| A2780 | 3 | Q2Dx13 | 36.65 (<0.05 to <0.01) | 58.6 (<0.0001) |
| A2780 | 1.5 | QDx26 | 33.36 (<0.05 to <0.01) | 59.0 (<0.0001) |
| SW480 | 8 | (Mon, Wed, Fri)x5 | 61.00 (<0.0001) | 72.5 (= 0.0002) |
| HCT 116 | 8 | (Mon, Wed, Fri)x4 | 37.58 (<0.05 to <0.01) | 73.0 (= 0.0005) |
| U-87 MG | 8 | (Mon, Wed, Fri)x4 | 53.33 (<0.0001) | 87.8 (<0.0001) |
| A-375 | 8 | (Mon, Wed, Fri)x4 | 28.47 (NS) | 77.5 (<0.0001) |
| K-562 | 8 | (Mon, Wed, Fri)x4 | 54.96 (<0.01 to <0.001) | 47.6 (<0.0001) |
| HEL 92.1.7 | 8 | Q2dx14 | 7.20 (NS) | 56.7 (<0.0001) |
| EL1997 | 10 / 8 | (Q2Dx7), 11-days OFF, (Mon, Wed, Fri)x4 | 80.28 (<0.0001) | 67.9 (<0.0001) |
| EL1989 | 10 / 8 | (Q2Dx7), 11-days OFF, (Mon, Wed, Fri)x3 | 70.42 (<0.0001) | 79.2 (<0.0001) |
| EL2144 | 10 | Q2Dx8 | 53.37(<0.0001) | ND* |
| EL2056 | 8 | (Mon, Wed, Fri)x5 | 59.05 (<0.0001) | 83.5 (<0.0001) |
| EL1986 | 8 | (Mon, Wed, Fri)x5 | 62.00 (<0.0001) | 84.9 (<0.0001) |

*Not Determined

The data in Table 2 evidences the tumor growth inhibition, and the inhibition of N1ICD cleavage by Compound 1 in various xenograft models of human tumor. The data in Table 2 further provides an in vivo correlation to the functional activity cell data described in Table 1.

Metabolism and Excretion

Compounds that demonstrate low or no Cytochrome P450 (CYP450) metabolism and modulation have a reduced likelihood for adverse interactions with other medications the patient is taking that could result in dose changes or a need to stop medication altogether. When CYP450 metabolism leads to appreciable exposure of patients to active metabolites, efficacy and safety issues can arise from the greater variability associated with the contribution of multiple active species; therefore, generally a drug lacking active metabolites is preferred. Therapeutic agents evidencing low or no CYP450 metabolism and modulation are desirable and may have superior safety profiles in and for patients. Lynch et al., *Am. Fam. Physician,* 76, 391 (2007). The potential for CYP450 enzyme interactions cannot be predicted based solely on the structure of an active pharmaceutical agent.

Compound 1 is not an inhibitor or inducer of the major CYP450 enzymes and was not metabolized to any appreciable extent by liver microsomes optimized for oxidative CYP450 metabolism. In rats and dogs in vivo, major oxidative metabolites were not observed in circulation or excreta. Therefore, Compound 1 has a low likelihood for CYP450-based interactions with other medications that could result in dose adjustments or a need to limit or stop additional medications in a patient being treated for cancer.

Compound 1 was evaluated in vivo in bile-duct cannulated rats to study systemic pharmacokinetics (PK), excretion, and metabolism. In vivo 51% of the IV dose was excreted unchanged, predominately in the urine, with low (2% of parent) systemic exposure to an active N-dealkylated metabolite, 4,4,4-trifluoro-N-[(1S)-1-methyl-2-oxo-2-[[(7S)-6-oxo-5,7-dihydropyrido[2,3-d][3]benzazepin-7-yl]amino]ethyl]butanamide. Profiling of rat plasma for metabolites, indicated the absence of additional circulating metabolites. Further studies in bile-duct intact dogs also supported appreciable clearance by excretion of parent compound, as well as the absence of major circulating active metabolites.

Overall metabolism and excretion data for Compound 1 evidenced desirable clearance mechanisms (urinary excretion of parent compound and amide hydrolysis to an inactive and non-circulating fragment, which is not formed in incubations with liver microsomes optimized for CYP450 metabolism), as well as the absence of major active circulating metabolites.

In the clinical setting, the clearance properties of Compound 1 observed preclinically are desirable. Compounds eliminated primarily by oxidative metabolism are known to exhibit variable exposure due to drug interactions with concomitant medications and certain fruit juices/herbs, liver disease, and inter-patient differences in enzyme activity. Multiple clearance mechanisms are preferred, because they diminish the impact of drug interactions occurring at any one elimination pathway. Therefore, clearance of Compound 1 by both excretion (51%) and metabolism (amide hydrolysis), without production of major active circulating metabolites, is advantageous to the patient. Overall these clearance properties decrease the likelihood for clinical dose adjustments, as well as minimize safety and efficacy concerns associated with major active circulating metabolites, administration of concomitant medications, and inter-patient differences in CYP450 activity.

We claim:

1. A compound of the structure:

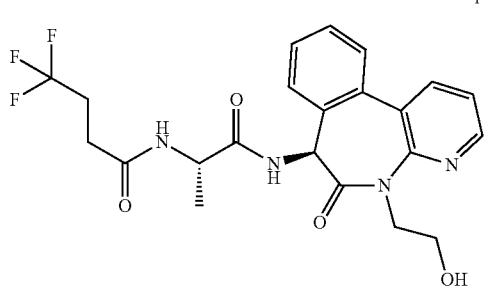

Compound 1 or a pharmaceutically acceptable salt or hydrate thereof.

2. A pharmaceutical composition comprising a compound of claim 1, or a pharmaceutically acceptable salt or hydrate thereof, in association with a pharmaceutically acceptable carrier.

3. A method of treating a cancer which is T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer or medulloblastoma in a patient comprising administering to a patient in need thereof a therapeutically effective amount of a compound of claim 1, or a pharmaceutically acceptable salt or hydrate.

4. A method of treating a cancer which is T-cell acute lymphoblastic leukemia, acute lymphoblastic leukemia, chronic myelogenous leukemia, erythroleukemia, breast cancer, ovarian cancer, melanoma, pancreatic cancer, glioblastoma or colorectal cancer in a patient comprising administering to a patient in need thereof a therapeutically effective amount of a compound of claim 1, or a pharmaceutically acceptable salt or hydrate thereof.

5. A crystalline hydrate of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide characterized by an X-ray powder diffraction pattern using CuKα radiation having a peak at 22.97±0.2 degrees 2-theta in combination with one or more peaks at 11.96±0.2, 18.81±0.2, 20.78±0.2 or 21.07±0.2 degrees 2-theta at ambient temperature and relative humidity.

6. A pharmaceutical composition comprising a compound of claim 5, in association with a pharmaceutically acceptable carrier.

* * * * *

SEQUENCE LISTING

```
<160> NUMBER OF SEQ ID NOS: 1

<210> SEQ ID NO 1
<211> LENGTH: 23
<212> TYPE: PRT
<213> ORGANISM: Artificial Sequence
<220> FEATURE:
<223> OTHER INFORMATION: signal peptide
```

```
<400> SEQUENCE: 1

Met Pro Arg Leu Leu Thr Pro Leu Leu Cys Leu Thr Leu Leu Pro Ala
1               5                   10                  15

Leu Ala Ala Arg Gly Leu Arg
                20
```